United States Patent [19]

Frantzides

[11] Patent Number: 5,439,476
[45] Date of Patent: Aug. 8, 1995

[54] INFLATABLE LAPAROSCOPIC RETRACTOR

[75] Inventor: Eleni C. Frantzides, Wauwatosa, Wis.

[73] Assignee: Trigonon, Inc., Wauwatosa, Wis.

[21] Appl. No.: 13,806

[22] Filed: Feb. 4, 1993

[51] Int. Cl.⁶ .................... A61H 29/00; A61M 29/02
[52] U.S. Cl. ...................... 606/192; 604/96; 600/207
[58] Field of Search ............... 128/20; 604/96, 99, 604/103; 606/190, 191, 192, 194, 198

[56] References Cited

U.S. PATENT DOCUMENTS

| | | | |
|---|---|---|---|
| Re. 29,207 | 5/1977 | Bolduc et al. . | |
| 638,367 | 12/1899 | Tuttle . | |
| 1,213,005 | 1/1917 | Pillsbury . | |
| 2,892,458 | 6/1959 | Auzin . | |
| 3,081,773 | 3/1963 | Isaac | 606/192 |
| 3,841,304 | 10/1974 | Jones | 606/192 |
| 3,882,852 | 5/1975 | Sinnreich | 606/192 |
| 4,292,974 | 10/1981 | Fogarty et al. | 606/194 |
| 4,299,227 | 11/1981 | Lincoff | 606/192 |
| 4,312,353 | 1/1982 | Shahbabian | 606/192 |
| 4,349,033 | 9/1982 | Eden . | |
| 4,555,242 | 11/1985 | Saudauger | 606/192 |
| 4,575,371 | 3/1986 | Nordqvist et al. . | |
| 4,619,247 | 10/1986 | Inoue et al. . | |
| 4,655,745 | 4/1987 | Corbett | 604/96 |
| 4,686,985 | 8/1987 | Lottick | 606/192 |
| 4,823,815 | 4/1989 | Watson et al. . | |
| 4,927,412 | 5/1990 | Menasche . | |
| 4,966,583 | 10/1990 | Debbas | 606/192 |
| 5,002,557 | 3/1991 | Hasson | 606/191 |
| 5,011,488 | 4/1991 | Ginsburg . | |
| 5,062,847 | 11/1991 | Barnes | 606/198 |
| 5,112,303 | 5/1992 | Pudenz . | |
| 5,163,949 | 11/1992 | Bonutti | 606/192 |
| 5,188,630 | 2/1993 | Christoudias | 604/1 |
| 5,195,507 | 3/1993 | Bilweis | 128/20 |
| 5,197,948 | 3/1993 | Ghodsian . | |
| 5,197,971 | 3/1993 | Bonnutti | 606/192 |
| 5,269,753 | 12/1993 | Wilk . | |
| 5,308,327 | 5/1994 | Heaven et al. . | |
| 5,318,586 | 6/1994 | Ereren . | |

FOREIGN PATENT DOCUMENTS

| | | | |
|---|---|---|---|
| 0490714A1 | 6/1992 | European Pat. Off. . | |
| 2529083 | 12/1983 | France . | |
| 208444 | 3/1909 | Germany | 604/99 |
| 1069823 | 10/1958 | Germany . | |
| WO92/21291 | 12/1992 | WIPO . | |
| WO92/21295 | 12/1992 | WIPO . | |

Primary Examiner—Stephen C. Pellegrino
Assistant Examiner—Nancy Mulcare
Attorney, Agent, or Firm—Miller & Christenbury

[57] ABSTRACT

A medical instrument for effective atraumatic retraction of abdominal organs during laparoscopic surgery is described. The device consists of a rigid rod with a bore running from an air valve at the proximal end to multiple perforations at the distal end of the rod. An inflatable balloon covers the multiple perforations on the distal end of the rod. The balloon is constructed from a relatively stiff plastic material, and it is firmly attached to the rod, such that the balloon inflates in substantially one direction in order to provide a relatively wide palmated anterior surface, and a relatively narrow cross-section. The outer surface is smooth, and may be further covered with a soft nylon mesh, in order to provide a wide, soft, atraumatic surface for retraction. The device may also include an introducer tube for passing the balloon through a laparoscopic cannula.

12 Claims, 4 Drawing Sheets

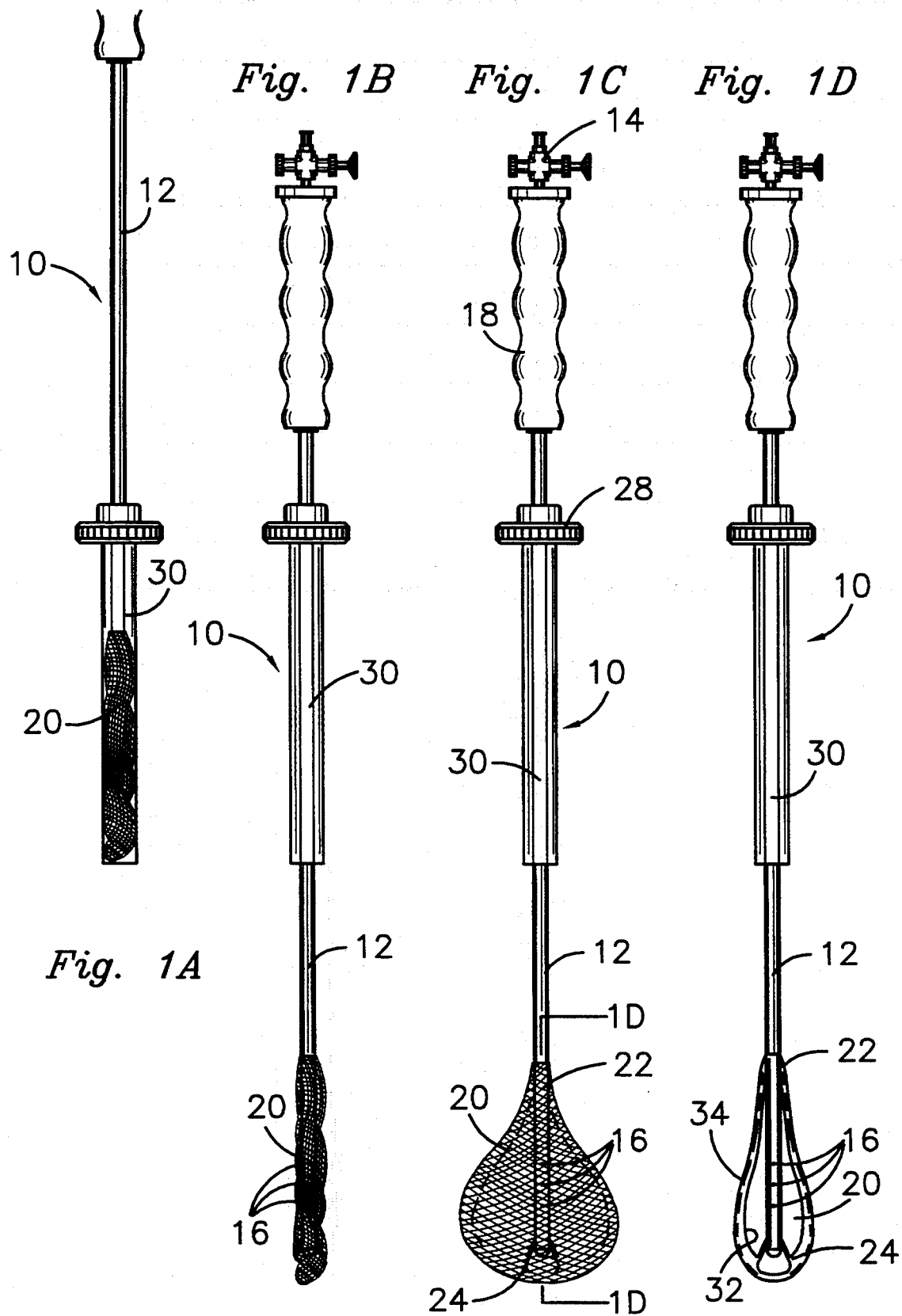

INFLATABLE LAPAROSCOPIC RETRACTOR

BACKGROUND OF THE INVENTION

1. Field of the Invention

This invention relates to an atraumatic retraction device for use in laparoscopic surgery. In particular, the invention relates to an inflatable medical device which may be inserted into the patient's abdomen through a small incision, inflated for use to retract an internal organ, then deflated and removed at the conclusion of the surgery.

2. Background of the Related Technology

Surgery on abdominal organs has traditionally been conducted through a single standard incision in the patient's abdomen. This technique is known as open surgery. During the last several years, less traumatic techniques have been developed to treat abdominal ailments, including laparoscopic surgery.

Laparoscopic surgery is performed through very small incisions in the abdomen, usually only 5 to 12 mm. The abdomen is inflated with carbon dioxide ($CO_2$)—a harmless gas—in order to expand the abdominal cavity to provide a space to perform the surgery. A laparoscope containing a camera inserted through a small incision in the navel enables the surgeon to inspect the inside of the abdomen on a television monitor. The entire surgery is conducted by the surgeon manipulating specially designed instruments which protrude into the abdomen through several other small incisions while the surgeon views the procedure on the television monitor.

This minimally invasive surgical technique has several advantages over traditional open surgery. Laparoscopic surgery usually takes less time than a comparable open surgery. Because no muscles are cut and only small incision are made, the patient is likely to experience less post-operative pain than from open surgery. The recovery time in the hospital, and therefore the cost, is often less. Furthermore, when the tiny incisions heal, the scars may be nearly invisible, instead of a long abdominal scar which usually results from open surgery.

Laparoscopic surgery, however, is still quite new and efficient retraction of abdominal organs has been challenging. One typical complication which often occurs during laparoscopic surgery is injury or hemorrhaging caused by contact of a surgical instrument against a fragile organ such as the liver or spleen. The small incisions through which laparoscopic surgery is performed severely limits the size and shape of retraction devices which may be used. Retraction devices currently used in laparoscopic surgery include mechanically expandable devices such as the three-pronged liver retractor (Cabot Medical Corp., Langhorne, Pa., U.S.A.) shown in FIG. 3. This particular device consists of a set of three metal prongs which may be collapsed together for insertion into the abdomen, then mechanically expanded within the abdominal cavity in order to retract the liver.

SUMMARY OF THE INVENTION

The invention disclosed herein is an inflatable medical device which provides atraumatic retraction of abdominal organs during laparoscopic surgery.

The device comprises an inflatable balloon attached to one end of a rigid rod or catheter. When the balloon is deflated, the device is small enough to be inserted into the abdomen through a small laparoscopic incision. Once inside the abdominal cavity, the balloon is inflated by injecting air into the opposite end of the rod. The balloon is specially constructed in that it inflates in substantially one direction to provide a wide "palmated" surface. The balloon is fixed to the rod in such a way that it provides a firm instrument for retracting internal organs. The balloon is constructed from a soft material to provide an atraumatic retracting surface, thereby substantially reducing the risk of injury to a fragile organ. After the surgery is completed, the balloon is deflated and removed.

The primary objects of the invention are therefore to provide an inflatable retraction device for use during laparoscopic surgery; to provide a device which is small enough to fit through a typical laparoscopic incision, yet expandable to provide a sufficiently large surface for retracting internal organs; and to provide an atraumatic method for retracting organs during laparoscopic surgery or thoracoscopic surgery.

Other objects and advantages of the invention will become apparent from the following description which sets forth, by way of illustration and example, certain preferred embodiments of the invention.

BRIEF DESCRIPTION OF THE DRAWINGS

The drawings, which constitute a part of the specification and include exemplary embodiments of the present invention, including the following:

FIG. 1 is a set of four views of an inflatable laparoscopic retraction device constructed in accordance with the principles of the invention. FIG. 1 shows a first embodiment of the invention which includes a soft nylon mesh covering the outer surface of the balloon. In particular:

FIG. 1A is a side view of the device showing the balloon deflated and packed inside of an introducer tube. It is in this configuration that the device is passed through a laparoscopic cannula.

FIG. 1B is a side view of the device after it has been inserted into the abdominal cavity, and the balloon has been extended out from the introducer tube.

FIG. 1C is a front view of the device with the balloon inflated and showing the wide palmated, anterior surface of the balloon.

FIG. 1D is a side view, partially in section, showing the narrow width of the inflated balloon.

FIG. 2 is a set of four views of a second embodiment of the invention in which the balloon is constructed with a single layer of material having a smooth outer surface. In particular:

DETAILED DESCRIPTION OF THE INVENTION

Figures 2A, 2B, 2C, 2D:
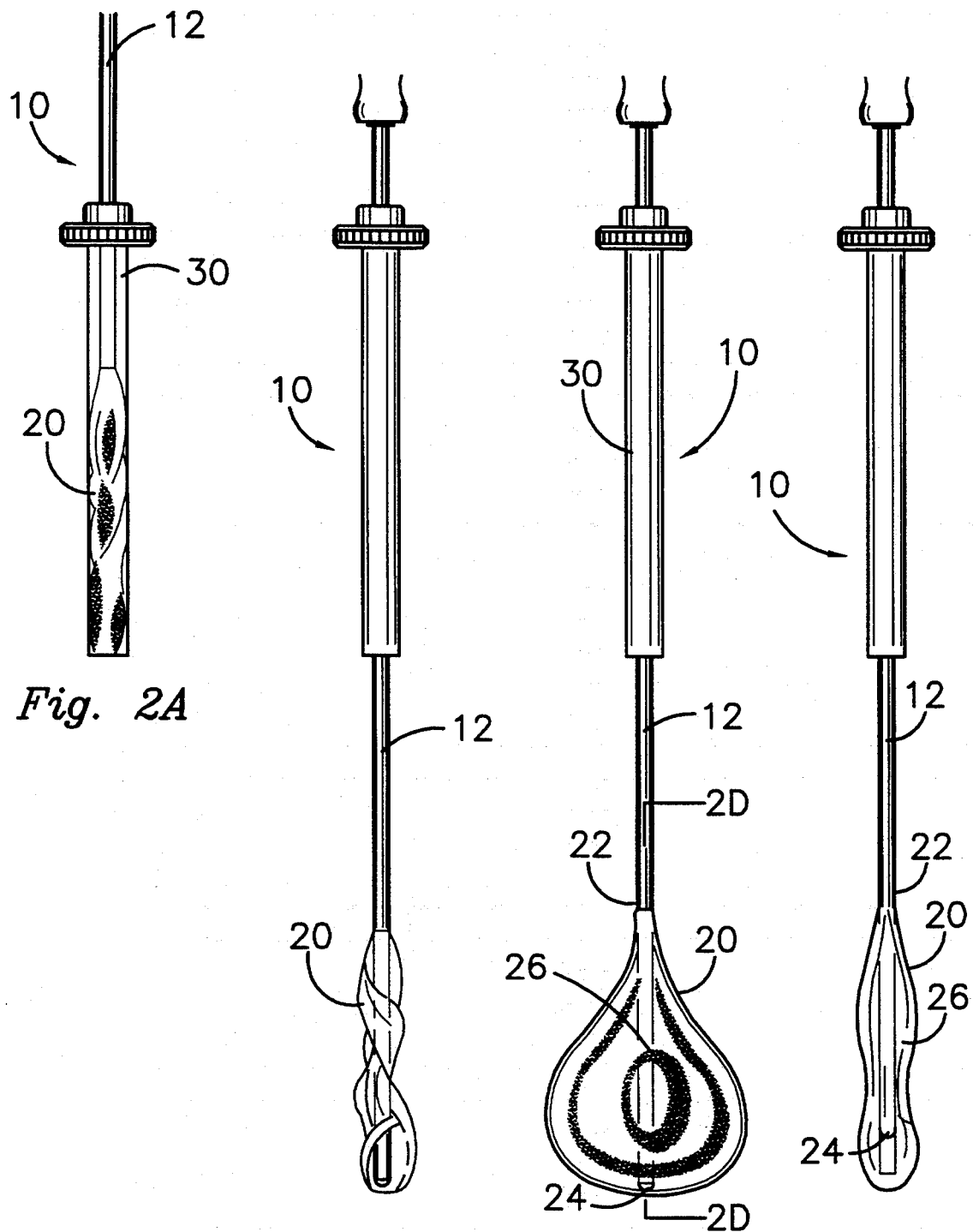
FIG. 2A is a side view showing the balloon packed inside an introducer tube.
FIG. 2B is a side view showing the balloon extended from the introducer tube.
FIG. 2C is a front view showing the wide anterior surface of the balloon.
FIG. 2D is a side view, partially in section, showing the narrow width of the balloon.
Figure 3:
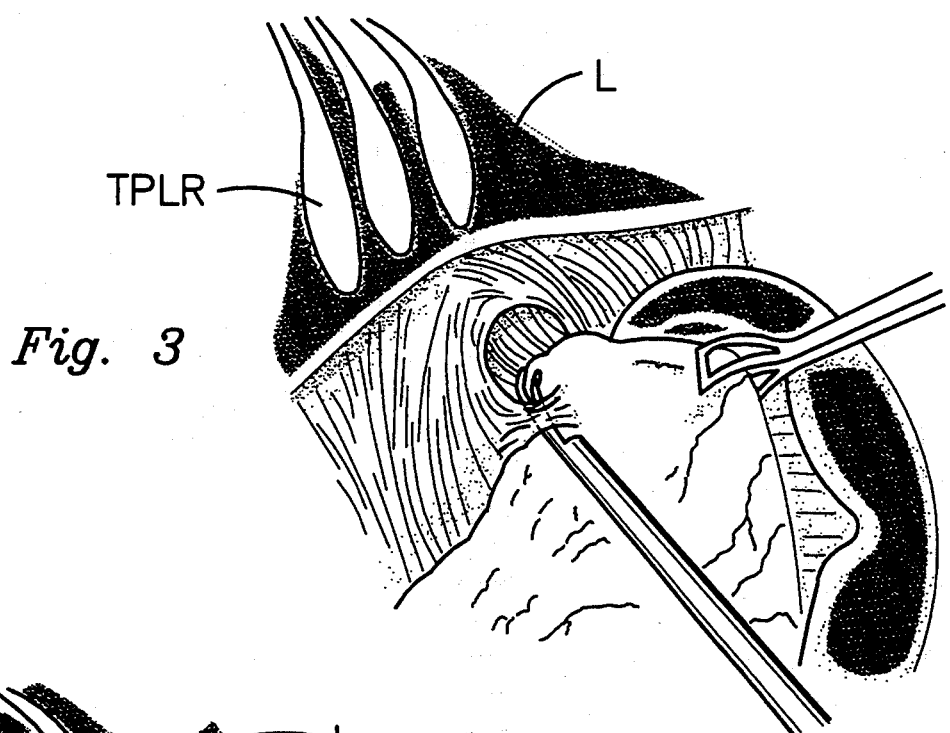
FIG. 3 shows a three-pronged liver retractor (TPLR) currently available on the market.

The present invention is essentially comprised of a specially constructed balloon firmly attached to the end of a rod. The following is a detailed description of the device itself, followed by description of how to make the device and by description of a method of using the device in laparoscopic surgery.

1. Inflatable Laparoscopic Retractor

A laparoscopic retraction device 10 according to the invention comprises a firm rod 12 with a single lumen or bore running completely through it from end to end. The rod may be constructed from either metal or a rigid plastic material. A valve or stopcock 14 is attached to the proximal end of the rod 12. Multiple perforations 16 are formed in the distal end of the rod 12.

An inflatable balloon 20 is fixed on the distal end of rod 12, covering the multiple perforations 16. The balloon 20 is made of a relatively compliant material such as a silicon sheath, polyvinylchloride, rubber, urethane, polyurethane, or other plastic.

The device further comprises an introducer tube 30, which is essentially a hollow tube. The rod 12 on which the balloon 20 is attached is slidable within and relative to the introducer tube 30. In other words, the rod 12 on which the balloon 20 is attached is slidable in a direction along the axis of the introducer tube 30. When deflated, the balloon 20 may be twisted and compacted so that it to fits within the introducer tube 30 as shown in FIGS. 1A and 2A.

The balloon 20 is uniquely constructed in that it inflates in substantially one direction. When inflated, the balloon 20 has a shape similar to that of a flattened tulip bulb or teardrop. Viewed anteriorly the balloon 20 has a wide "palmated" appearance. That is, viewed from the front the balloon 20 presents a broad substantially flat surface (front and back) as shown in FIGS. 1C and 2C. Viewed from the side, the inflated balloon 20 has relatively narrow cross-section as shown in FIGS. 1D and 2D.

The balloon 20 is fixed to the rod 12 in at least two places in order to firmly hold the balloon 20 in place with respect to the rod 12. As shown in FIGS. 1C and 1D and in FIGS. 2C and 2D, an upper central portion 22 of the balloon is attached to and sealed to the outer circumference of the rod at a point above the perforations 16. The lower central portion 24 of the balloon is attached to the distal end of the rod 12. To provide an even firmer connection, a third point of connection may be made by attaching the middle portion 26 of the balloon 20 to the rod 12 as shown in FIGS. 2C and 2D. If the balloon 20 were not attached to at least two points of the rod 12, the balloon 20 would flip freely back and forth, and thus not provide the firmness necessary to retract an organ.

The balloon 20 is made from a material which will not cause injury to internal organs under normal usage. FIG. 2 shows a balloon made from a single layer 32 of material having a very smooth outer surface, e.g., plastic. FIG. 1 shows a two-layered balloon, with the outer layer comprising a covering of mesh 34 made of nylon or other additive like cotton in order to provide a soft texture to the outer surface of the balloon 20.

A handle 18 on the proximal end of the rod 12 and a finger wheel 28 on the proximal end of the introducer tube 30 facilitate handling the device 10 during surgery.

2. Fabrication of the Balloon

One of the unique features of the device 10 lies in the nature of the construction of the balloon 20 so that it inflates more so in one direction than the other. Such a balloon 20 may be constructed by placing a first sheet of material (plastic or a silicon sheath) onto a flat surface. The distal end of the rod 12 is placed over the first sheet of material. A second sheet of material is then laid over the rod so that the rod is sandwiched between the two sheets. The two layers of material are cut in the shape of a bulb or teardrop, and the edges of the two sheets are sealed together with silicon gel. The upper central portion 22 of the balloon 20 (i.e., the upper tip of the teardrop) is wrapped tightly against the outer circumference of the rod 12 with a suture, and sealed with silicon gel.

The nylon mesh 34 may also be applied with two sheets. That is, a first layer of nylon mesh is laid on a flat surface. The mesh is also held in a stretched state. The device 10, with the first layer 32 of the balloon 20 having already been constructed as described above, is laid over the first layer of nylon mesh. A second layer is then laid over the device, and the second layer is also stretched. The two layers of mesh may then be cut and stitched to the outer edge of the plastic layers of the balloon 20 (i.e., stitched along the outline of the teardrop). The stitches may be sealed with silicon gel.

The distal end of the rod may be fixed to the lower central portion 24 of the balloon by inserting into the balloon a hypodermic needle filled with silicon gel. The silicon gel is applied to the end of the rod 12 and to the inner surface of the balloon 20. When the hypodermic needle is withdrawn, additional silicon gel is extracted, thereby sealing the hole in the balloon 20 which would otherwise result from the hypodermic needle. The middle portion 26 of the balloon may be connected to the rod as shown in FIG. 2D by again injecting silicon gel into the balloon at the proper location.

By stretching the nylon mesh 34 during fabrication, the nylon mesh is stretched tight when the balloon 20 is inflated, otherwise the mesh would slide relative to the inner plastic layer 32.

3. Use During Surgery

Figure 4:
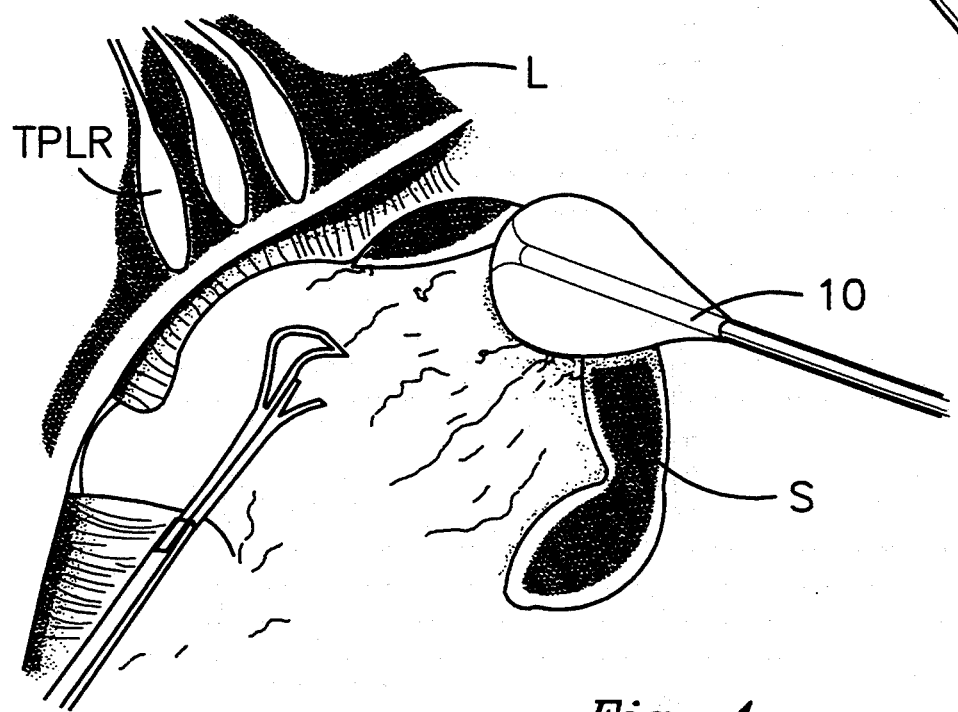
FIG. 4 shows the present invention of an inflatable laparoscopic device being used to retract a spleen (S) (a three-pronged liver retractor is also shown).
Figure 5:
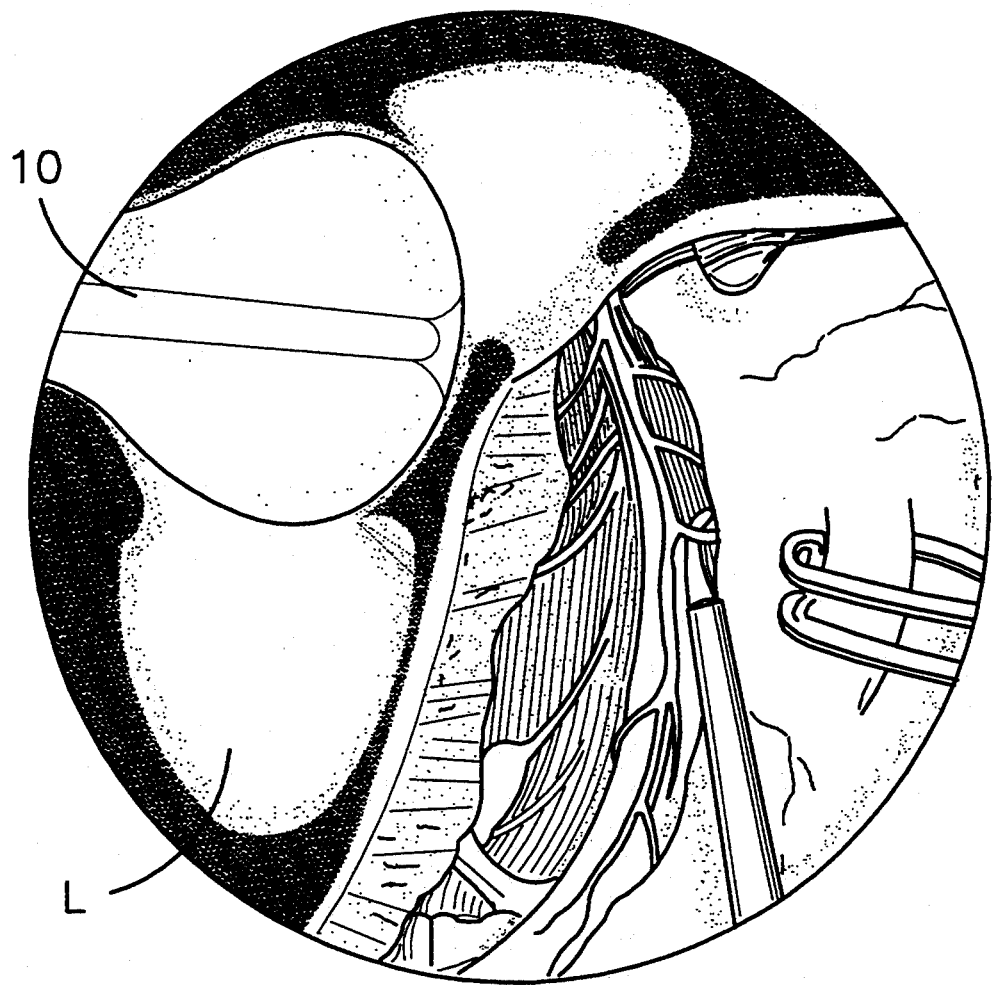
FIG. 5 shows the present invention of an inflatable laparoscopic retraction device being used to retract a liver (L).

The laparoscopic retractor 10 is provided initially with the inflatable balloon 20 contained within the introducer tube 30 as shown in FIGS. 1A and 2A. The introducer tube 30 is passed through a laparoscopic trocar and cannula into the abdominal cavity. When proper position is attained, the balloon 20 is extracted by sliding the rod 12 downward relative to the introducer tube 30 as shown in FIGS. 1B and 2B. The balloon 20 is inflated by injecting air or water through the valve or stopcock 14 on the proximal end of the rod 12. The fluid passes through the rod 12 and inflates the balloon 20 on the distal end of the rod. The device 10 with the balloon inflated as shown in FIGS. 1C and 1D and FIGS. 2C and 2D, is then ready for use as a retraction instrument. Abdominal or thoracic organs may be retracted as desired by manipulating the proximal end of the rod in the proper manner. The device 10 is shown being used to retract a liver L and spleen S in FIGS. 4 and 5, respectively.

When the surgery is completed, the balloon 20 may be deflated by ejecting the fluid from the balloon 20 out through the stopcock 14. The balloon 20 is then replaced within the introducer tube 30, and the entire device 10 removed from the abdominal cavity.

Finally, it is recognized that the present invention may be constructed in a number of configurations, all of which satisfy the primary objective of providing an inflatable, atraumatic laparoscopic retraction device. The invention described above may be used in a wide variety of applications using traditional trocar and cannula designs which presently range from about 5–12 millimeters. Of course, the dimensions of the device and the specific shape, particularly of the balloon, may be specially adapted to address particular circumstances.

Therefore, specific details of the invention disclosed above are not to be interpreted as limiting, but merely as a basis for the claims and for teaching one skilled in the art to variously practice and construct the present invention in any appropriately detailed manner. Changes may be made in details of construction of the invention without departing from the spirit of the invention, especially as defined in the following claims.

I claim as my invention:

1. An inflatable laparoscopic retraction device for atraumatic retraction of internal organs comprising:
   an introducer tube insertable longitudinally into and removable longitudinally from a cannula;
   a rigid rod movable longitudinally back and forth in said introducer tube, said rod having an outer surface having a size and shape for extending said rod into and through said introducer tube, said rod further having a bore running from a proximal end to a distal end of said rod for transmitting fluid therethrough;
   said rod having a perforated portion at a location adjacent said distal end for transmitting fluid from said bore in said rod to said outer surface of said rod;
   an inflatable balloon affixed tightly upon said outer surface of said rod at a location spaced from said distal end and there attached for covering said perforated portion of said rod, said balloon having a body portion extending along said outer surface of said rod and attached adjacent to said distal end of said rod, said balloon being wrappable around said outer surface of said rod and said balloon having an outer layer of mesh positioned for atraumatic contact with said internal organs, said balloon when inflated having a relatively broad surface when viewed in a first plane parallel to an axis of said rod and having a relatively narrow surface when viewed in a second plane 90° from said first plane and parallel to said axis; and
   means for injecting fluid into or withdrawing fluid from said bore of said rod and thereby inflating said balloon after it has been extended through said introducer tube and said cannula and for deflating said balloon for subsequent re-wrapping of said balloon on said outer surface of said rod between said outer surface of said rod and an inside surface of said introducer tube, and for withdrawal of said introducer tube, said balloon and said rod from said cannula.

2. The laparoscopic retraction device of claim 1 wherein said balloon is bulb shaped and when inflated has a larger diameter at said distal end than its diameter at said point of attachment spaced from said distal end and having a non-circular cross-section when viewed along an axis of said rod.

3. The laparoscopic retraction device of claim 1, wherein said outer layer of mesh positioned on said balloon is a nylon mesh.

4. The laparoscopic retraction device of claim 1, wherein said outer layer of mesh positioned on said balloon is stretched tight when said balloon is inflated.

5. The laparoscopic retraction device of claim 4, wherein said outer layer of mesh positioned on said balloon cannot move relative to said balloon when said balloon is inflated.

6. The laparoscopic retraction device of claim 1, wherein said outer layer of mesh positioned on said balloon comprises two sheets of mesh.

7. An inflatable laparoscopic retraction device for atraumatic retraction of internal organs comprising:
   an introducer tube insertable longitudinally into and removable longitudinally from a cannula;
   a rigid rod movable longitudinally back and forth in said introducer tube, said rod having an outer surface sized and shaped for extending said rod into and through said introducer tube, said rod also having a bore running from a proximal end of said rod to a distal end of said rod for transmitting fluid therethrough, said rod further having a perforated portion at a location adjacent said distal end of said rod for transmitting fluid from said bore in said rod to said outer surface of said rod;
   an inflatable balloon having a proximal end portion sealably affixed to said outer surface of said rod at a location between said perforated portion of said rod and said proximal end of said rod, said inflatable balloon also having a distal end portion attached adjacent to said distal end of said rod, said inflatable balloon further having a body portion extending from said proximal end portion of said balloon to said distal end portion of said balloon for covering said perforated portion of said rod, said body portion of said inflatable balloon having an outer layer of mesh positioned for atraumatic contact with said internal organs; and
   means for injecting fluid into or withdrawing fluid from said bore of said rod and thereby inflating said balloon after it has been extended through said introducer tube and said cannula and deflating said balloon for replacement within said introducer tube and for withdrawal of said introducer tube with said balloon and said rod from said cannula, said balloon when inflated having a relatively broad surface when viewed in a first plane parallel to an axis of said rod and having a relatively narrow surface when viewed in a second plane 90° from said first plane and parallel to said axis, and said balloon when deflated having a size and shape for wrapping around said outer surface of said rod and for insertion into said introducer tube.

8. The laparoscopic retraction device of claim 7, wherein a portion of said body of said balloon is further attached to said rod.

9. The laparoscopic retraction device of claim 7, wherein said outer layer of mesh positioned on said body portion of said balloon is a nylon mesh.

10. The laparoscopic retraction device of claim 7, wherein said outer layer of mesh positioned on said body portion of said balloon is stretched tight when said balloon is inflated.

11. The laparoscopic retraction device of claim 10, wherein said outer layer of mesh positioned on said body portion of said balloon cannot move relative to said balloon when said balloon is inflated.

12. The laparoscopic retraction device of claim 7, wherein said outer layer of mesh positioned on said body portion of said balloon comprises two sheets of mesh.

* * * * *